US007037496B2

(12) United States Patent
Ghrayeb et al.

(10) Patent No.: US 7,037,496 B2
(45) Date of Patent: May 2, 2006

(54) CHIMERIC IMMUNOGLOBULIN FOR CD4 RECEPTORS

(75) Inventors: John Ghrayeb, Thorndale, PA (US); David M. Knight, Berwyn, PA (US); James E. Looney, Irving, CA (US)

(73) Assignee: Centocor, Inc., Radnor, PA (US)

( * ) Notice: Subject to any disclaimer, the term of this patent is extended or adjusted under 35 U.S.C. 154(b) by 302 days.

(21) Appl. No.: 09/896,050

(22) Filed: Jun. 29, 2001

(65) Prior Publication Data

US 2001/0051709 A1    Dec. 13, 2001

Related U.S. Application Data

(63) Continuation of application No. 07/867,100, filed as application No. PCT/US90/07671 on Dec. 27, 1990, now abandoned, which is a continuation-in-part of application No. 07/457,389, filed on Dec. 27, 1989, now abandoned.

(51) Int. Cl.
*A61K 39/395* (2006.01)
*C07K 16/28* (2006.01)

(52) U.S. Cl. .............................. 424/133.1; 424/143.1; 424/144.1; 424/154.1; 424/173.1; 424/801; 424/809; 530/387.3; 530/387.1; 530/388.2; 530/388.22; 530/385.75; 530/867; 530/866

(58) Field of Classification Search ............ 530/387.3, 530/387.1, 388.2, 388.22, 388.75, 866, 867; 424/133.1, 143.1, 144.1, 154.1, 173.1, 801, 424/809
See application file for complete search history.

(56) References Cited

U.S. PATENT DOCUMENTS

| 4,381,295 A | 4/1983 | Kung et al. |
| 4,695,459 A | 9/1987 | Steinman et al. |

FOREIGN PATENT DOCUMENTS

| EP | 0 125 023 A1 | 11/1984 |
| EP | 0 171 496 A2 | 2/1986 |
| EP | 0 173 494 A2 | 3/1986 |
| EP | 0 200 412 A2 | 12/1986 |
| EP | 0 240 344 B1 | 10/1987 |
| EP | 0 365 209 A2 | 4/1990 |
| EP | 0 394 827 | 10/1990 |
| EP | 0 511 308 B1 | 11/1992 |
| WO | WO 86/01533 A1 | 3/1986 |
| WO | WO 88/09181 | 12/1988 |
| WO | WO 90/12868 | 11/1990 |
| WO | WO 91/09966 | 7/1991 |
| WO | WO 91/09967 | 7/1991 |

OTHER PUBLICATIONS

Taylor et al., Chapter T4.14, from: "Leukocyte Typing III, White Cell Differentiation Antigens", Oxford University Press, 1987, pp. 234-237.*

Kong, Y. M., et al., "Pathogenic Mechanisms in Murine Autoimmune Thyroiditis: Short- and Long-Term Effects of in vivo depletion of CD4+ and CD8+ Cells," *Clin. Exp. Immunol.*, 77:428-433 (1989).

Cobbold, S.P., et al., "Therapy with Monoclonal Antibodies by Elimination of T-Cell Subsets in vivo," *Nature*, 312:548-551 (1984).

Mudgett-Hunter, M., et al., "Binding and Structural Diversity Among High-Affinity Monoclonal Anti-Digoxin Antibodies," *Molecular Immunology*, 22(4):477-488 (1985).

Playfair, J.H.L., "Antigen-Antibody Interaction and Immune Complexes," In *Immunology At a Glance*, (Blackwell Scientific Publication; London), Chapter 14 (1984).

Evans, R.L., et al., "Thymus-Dependent Membrane Antigens in Man: Inhibition of Cell-Mediated Lympholysis by Monoclonal Antibodies to $T_{H2}$ Antigen," *Proc. Natl. Acad. Sci.*, 78(1):544-548 (1981).

Matthews, T.J., et al., "AIDS Vaccines", *Scientific American*, 259(4):98-105 (1988).

van Oosten, B. W., et al., "Treatment of Multiple Sclerosis with the Monoclonal Anti-CD4 Antibody cM-T412: Results of a Randomized, Double-Blind, Placebo-Controlled, MR-Monitored Phase II Trial," *Neurology*, 49:351-357 (1997).

Moreland, L. W., et al., "Experience with a Chimeric Monoclonal Anti-CD4 Antibody in the Treatment of Refractory Rheumatoid Arthritis," *Clinical and Experimental Rheumatology*, 11(Suppl. 8):S153-S159 (1993).

(Continued)

*Primary Examiner*—Ronald B. Schwadron
(74) *Attorney, Agent, or Firm*—Hamilton, Brook, Smith & Reynolds, P.C.

(57) ABSTRACT

Chimeric antibodies for CD4 receptor comprising a variable or antigen binding region of a non-human origin specific for CD4 receptor and a constant region of human origin are disclosed. These antibodies are useful as therapeutic agents for auto-immune disorders.

9 Claims, 1 Drawing Sheet

OTHER PUBLICATIONS

Gill, H.S., et al., "In vivo Inhibition by a Monoclonal Antibody to CD4+ T Cells of Humoral and Cellular Immunity in Sheep," *Immunology*, 77:38-42 (1992).

Bushell, A., et al., "Transplantation Tolerance Induced by Antigen Pretreatment and Depleting Anti-CD4 Antibody Depends on CD4+ T Cell Regulation During the Induction Phase of the Response," *Eur. J. Immunol.*, 25:2643-2649 (1995).

Matloubian, M., et al., "CD4+ Cells are Required to Sustain CD8+ Cytotoxic T-Cell Responses During Chronic Viral Infection," *Journal of Virology*, 68(12):8056-8063 (1994).

Canva-Delcambre, V., et al., "Treatment of Severe Crohn's Disease with Anti-CD4 Monoclonal Antibody," *Ailment Pharmacol. Ther.*, 10:721-727 (1996).

van Montfrans, C., et al., "Immunotherapy of Crohn's Disease," *Mediators of Inflammation*, 7:149-152.

Reiter, C., et al., "Treatment of Rheumatoid Arthritis with Monoclonal CD4 Antibody M-T151. Clinical Results and Immunopharmacologic Effects in an Open Study, Including Repeated Administration," *Arthritis and Rheumatism*, 34(5): 525-536 (1991).

Moreland, L. W., et al., "Use of a Chimeric Monoclonal Anti-CD4 Antibody in Patients with Refractory Rheumatoid Arthritis," *Arthritis and Rheumatism*, 36(3):307-318 (1993).

Boehringer Mannheim Biochemicals Catalogue, p. 328, 1987/1988.

Boehringer Mannheim Biochemicals Catalogue, p. 109, 1989.

Genbank Accession No. PH1224, "Ig Kappa Chain Precursor V Region (M-T151)—Mouse (fragment)," (1999) [online], [retrieved on Apr. 10, 2000]. Retreived from www.ncbi.nlm.nih.gov:80.

Genbank Accession No. PH1225, "Ig Heavy Chain Precursor V Region (M-T151)—Mouse (fragment)," (1999) [online], [retrieved on Apr. 10, 2000]. Retreived from www.ncbi.nlm.nih.gov:80.

Genbank Accession No. S19970, "Ig Kappa Chain V Region (M-T151)—Mouse (fragment)," (1999) [online], [retrieved on Apr. 10, 2000]. Retrieved from www.ncbi.nlm.nih.gov:80.

Genbank Accession No. S19963, "Ig Heavy Chain V Region (M-T151)—Mouse)fragment)," (1996) [online], [retrieved on Apr. 10, 2000]. Retrieved from www.ncbi.nlm.nih.gov:80.

Genbank Accession No. CAA46223, "Alpha CD4 mAb Immunoglobulin Light Chain VJ Region [Mus musculus]," (1997) [online], [retrieved on Apr. 10, 2000]. Retrieved from www.ncbi.nlm.nih.gov:80.

Genbank Accession No. CAA46215, "Alpha CD4 mAb Immunoglobulin Heavy Chain VDJ Region [Mus Musculus]," (1997) [online], [retrieved on Apr. 10, 2000]. Retrieved from www.ncbi.nlm.nih.gov:80.

Genbank Accession No. AAB24319, "Anti-CD4 mAb M-T151 Variable Region Heavy Chain <J4, Chimeric Antibody> [Mice, Hybridoma Cells, Peptide Partial, 139 aa]," (1993) [online], [retrieved on Apr. 10, 2000]. Retrieved from www.ncbi.nlm.nih.gov:80.

Genbank Accession No. AAB24318, "Anti-CD4 mAb M-T151 Variable Region Light Chain [J2, Chimeric Antibody] [Mice, Hybridoma Cells, Peptide Partial, 127 aa]," (1993) [online], [retrieved on Apr. 10, 2000]. Retrieved from www.ncbi.nlm.nih.gov:80.

Genbank Accession No. X65095, "M. musculus mRNA for IG Light Chain VJ Region (M-T151)," (1997) [online], [retrieved on Apr. 10, 2000]. Retrieved from www.ncbi.nlm.nih.gov:80.

Genbank Accession No. X65087, "M. musculus mRNA for IG Heavy Chain VDJ Region (M-T151)," (1997) [online], [retrieved on Apr. 10, 2000]. Retrieved from www.ncbi.nlm.nih.gov:80.

Genbank Accession No. S50263, "Ig VH=anti-CD4 mAb M-T151 Variable Region Heavy Chaim <J4, Chimeric Antibody> [Mice, Hybridoma Cells, mRNA Partial, 417 nt]," (1993) [online], [retrieved on Apr. 10, 2000]. Retrieved from www.ncbi.nlm.nih.gov:80.

Genbank Accession No. S50261, "Ig VL=anti-CD4 mAb M-T151 Variable Region Light Chain <J2, Chimeric Antibody> [Mice, Hybridoma Cells, mRNA Partial, 381 nt]," (1993) [online], [retrieved on Apr. 10, 2000]. Retrieved from www.ncbi.nlm.nih.gov:80.

Declaration of Dr. Christian Reiter executed on Nov. 2, 1994, filed in opposition proceeding in EP 0 511 308 (Reference AL3).

Declaration of Dr. Margaret R. Dalesandro executed on Jul. 1, 1998, filed in opposition proceeding in EP 0 511 308 (Reference AL3).

Sun, L.K., et al., "Chimeric Antibody with Human Constant Regions and Mouse Variable Regions Directed Against Carcinoma-Associated Antigen 17-1A," *Proc. Natl. Acad. Sci. USA*, 84:214-218 (1987).

Morrison, S.L., et al., "Chimeric Human Antibody Molecules: Mouse Antigen-binding Domains with Human Constant Region Domains," *Proc. Natl. Acad. Sci. USA*, 81:6851-6855 (1984).

Landau, N.R., et al., "The Envelope Glycoprotein of the Human Immunodeficiency Virus Binds to the Immunoglobulin-like Domain of CD4," *Nature*, 334:159-162 (1988).

Wang, J., et al., "Atomic Structure of a Fragment of Human CD4 Containing Two Immunoglobulin-like Domains," *Nature*, 348:411-418 (1990).

Ryu, S.E., et al., "Crustal Structure of an HIV-binding Recombinant Fragment of Human CD4," *Nature*, 348:419-426 (1990).

Sattentau, Q.J., et al., "Epitopes of the CD4 Antigen and HIV Infection," *Science*, 234:1120-1123 (1986).

Peterson, A., et al., "Genetic Analysis of Monoclonal Antibody and HIV Binding Sites on the Human Lymphocyte Antigen CD4," *Cell*, 54:65-72 (1988).

Sattentau, Q.J., et al., "Structural Analysis of the Human Immunodeficiency Virus-binding Domain of CD4," *J. Exp. Med.*, 170:1319-1334 (1989).

Ashkenazi, A., et al., "Mapping the CD4 Binding Site for Human Immunodeficiency Virus by Alanine-Scanning Mutagenesis." *Proc. Natl. Acad. Sci. USA*, 87:7150-7154 (1990).

Healey, D., et al., "Novel Anti-CD4 Monoclonal Antibodies Separate Human Immunodeficiency Virus Infection and Fusion of CD4+ Cells From Virus Binding," *J. Exp. Med.*, 172:1233-1242 (1990).

Wofsy, D., et al., "Successful Treatment of Autoimmunity in NZB/.NZW $F_1$ Mice With Monoclonal Antibody to L3T4" *J. Exp. Med.*, 161:378-391 (1985).

Ranges, G.E., et al., "Prevention of Type II Collagen-induced Arthritis by in vivo Treatment with Anti-L3T4," *J. Exp. Med.*, 162:1105-1110 (1985).

Wofsy, D., "Administration of Monoclonal, Anti-T Cell Antibodies Retards Murine Lupus in BXSB Mice," *J. Immunol.*, 136(12):4554-4560 (1986).

Hafler, D.A., et al., "Anti-CD4 and Anti-CD2 Monoclonal Antibody Infusions in Subjects with Multiple Sclerosis," *J. Immunol.*, 141(1):131-138 (1988).

Hom, et al., "The Progression of the Inflammation in Established Collagen-Induced Arthritis can be Altered by Treatments With Immunological or Pharmacological Agents Which Inhibit T Cell Activities," *Eur. J. Immunol.*, 18:881-888 (1988).

Ermak, T.H., et al., "Treatment of Murine Lupus with Monoclonal Antibody to L3T4," *Laboratory Investigation*, 61(4):447-456 (1989).

Alters, S.E., "A Comparison of Rat and Rat-Mouse Chimeric Anti-Murine CD4 Antibodies for Use in Immunotherapy," (A Dissertation at Stanford University, May 1989).

Alters, S.E., et al., "Comparison of Rat and Rat-Mouse Chimeric Anti-Murine CD4 Antibodies for Use in Immunotherapy," *FASEB J.*, 3(3):A492, Abstract No. 1546 (1989).

Alters, S.E., et al., "Comparison of Rat and Rat-Mouse Chimeric Anti-Murine CD4 Antibodies in vitro," *J. Immunol.*, 142(6):2018-2023 (1989).

Alters, S.E., et al., "Mechanisms of Anti-CD4-Mediated Depletion and Immunotherapy—A Study Using a Set of Chimeric Anti-CD4 Antibodies," *J. Immunol.*, 144)12): 4587-4592 (1990).

Herzog, C., et al., "Monoclonal Anti-CD4 in Arthritis," *The Lancet*, 2 (8573):1461-1462 (1987).

Herzog, C., et al., "Anti-CD4 Antibody Treatment of Patients with Rheumatoid Arthritis: I. Effect on Clinical Course and Circulating T Cells," *J. Autoimmunity*, 2:627-642 (1989).

Walker, C., et al., "Anti-CD4 Antibody Treatment of Patients with Rheumatoid Arthritis: II. Effect of in vivo Treatment on in vitro Proliferative Response of CD4 Cells," *J. Autoimmunity*, 2:643-649 (1989).

Oi, V.T., et al., "Chimeric Antibodies," *BioTechniques*, 4(3) :214-221 (1986).

Morrison, S.L., et al., "Genetically Engineered Antibody Molecules: New Tools for Cancer Therapy," *Cancer Investigation*, 6(2) :185-192 (1988).

Wood, G.S., et al., "Immunopathology of Mycosis Fungoides (MF) Patients Treated with Chimeric Anti-CD4 Antibody," *J. Cutaneous Pathology*, 16(5) :330 (Abstract) (1989).

Knox, J., et al., "A Phase I Clinical Trial with Chimeric Anti-CD4 Monoclonal Antibody in Patients with Mycosis Fungoides," *J. Cell Biochem. -Suppl. 14* Part B:108, Abstract No. CE 513 (1990).

Reiter, C., et al., "In Vitro and In Vivo Characteristics of a Chimeric Human-Mouse Monoclonal CD4 Antibody," *Immunobiology*, 181 (213) :219-220 (1990).

Traunecker, A., et al., "Highly Efficient Neutralization of HIV with Recombinant CD4-Immunoglobulin Molecules," *Nature*, 339:68-70 (1989).

Waldmann, T.A., "Monoclonal Antibodies in Diagnosis and Therapy," *Science*, 252:1657-1662 (1991).

Harris, W.J., and S. Emery, "Therapeutic Antibodies—The Coming of Age," *TIBTECH*, 11:42-44 (1993).

Hird, V. and A.A. Epenetos, "Immunotherapy with Monoclonal Antibodies," In: *Genes and Cancer*, Carney, D. et al. Eds. (John Wiley & Sons Ltd.; New York), Chapter 17, pp. 183-189 (1990).

Dillman, R.O., "Human Antimouse and Antiglobulin Responses to Monoclonal Antibodies," *Antibody Immunoconjugates, and Radiopharmaceuticals*, 3 (1):1-15 (1990).

Benjamin, R.J. et al., "Tolerance to Rat Monoclonal Antibodies, Implications for Serotherapy," *J. Exp. Med.*, 163:1539-1552 (1986).

Herlyn, D. et al., "Specific Detection of Anti-Idiotypic Immune Responses in Cancer Patients Treated with Murine Monoclonal Antibody," *J. Immunol. Methods*, 85:27-38 (1985).

Shawler, D.L. et al., "Human Immune Response to Multiple Injections of Murine Monoclonal IgG," *J. Immunol.*, 135(2) :1530-1535 (1985).

Chatenoud, L. et al., "Restriction of the Human in vivo Immune Response Against the Mouse Monoclonal Antibody OKT3," *J. Immunol.*, 137(3):830-838 (1986).

Brüggemann, M. et al., "The Immunogenicity of Chimeric Antibodies," *J. Exp. Med.*, 170:2153-2157 (1989).

Khazeli, M.B. et al., "Pharmacokinetics and Immune Response of $^{131}$I-Chimeric Mouse/Human B72.3 (Human $_\gamma$4) Monoclonal Antibody in Humans," *Cancer Res.*, 51: 5461-5466 (1991).

Abbas A.K. et al., Cellular and Molecular Immunology, (W.B. Saunders Co.), p. 153 (1991).

Weissenhorn, W. et al., "Combinatorial Functions of Two Chimeric Antibodies Directed to Human CD4 and One Directed to the α-Chain of the Human Interleukin-2 Receptor," *Gene*, 121: 271-278 (1992).

Weissenhorn, W. et al., "Structural Diversity of Monoclonal CD4 Antibodies and Their Capacity to Block the HIV GP120/CD4 Interaction," *Hybridoma*, 15 (2) :117-124 (1996).

* cited by examiner

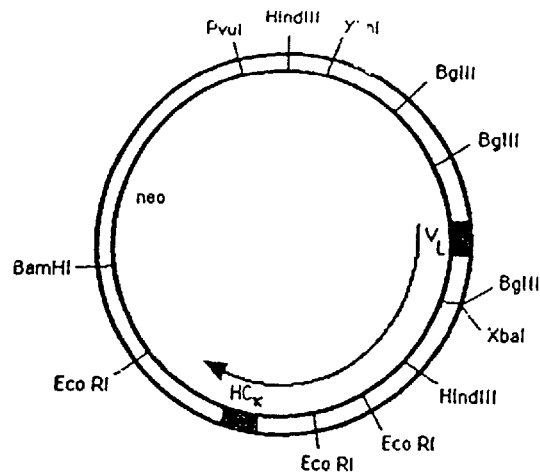
p412HuKcmneo
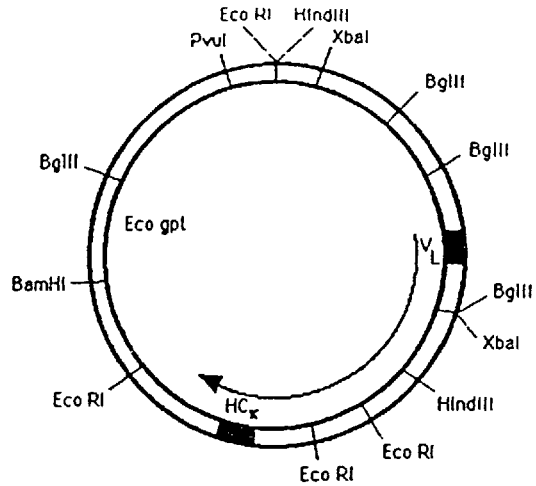
p412HuKapgpt
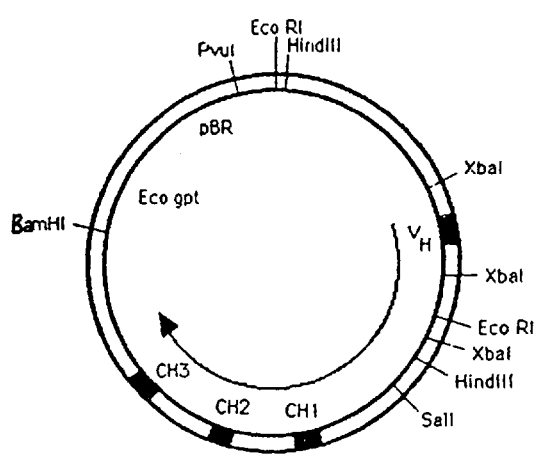
p412HG1apgpt
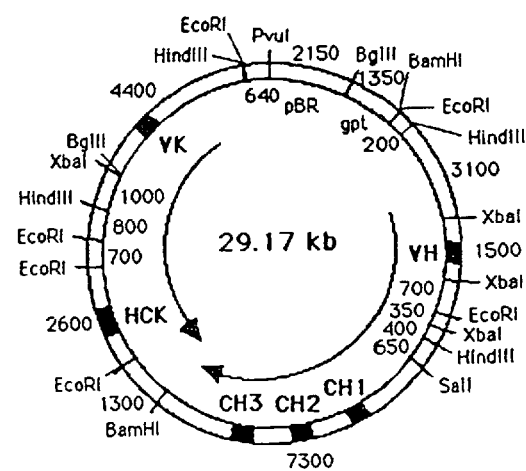
p412DP

CHIMERIC IMMUNOGLOBULIN FOR CD4 RECEPTORS

RELATED APPLICATIONS

This application is a continuation of application Ser. No. 07/867,100, filed May 2, 1994 (Abandoned), which is the U.S. National stage of International Application No. PCT/US90/07671, filed on Dec. 27, 1990, published in English, which is a Continuation-in-part of application Ser. No. 07/457,389, filed Dec. 27, 1989 (Abandoned). The entire teachings of the above applications are incorporated herein by reference.

BACKGROUND OF THE INVENTION

The nature of autoantigens responsible for autoimmune disorders is not known, nor is the action which triggers the autoimmune response. One theory involves the similarity of a viral protein to a self antigen, which results in autoreactive T cells or B cells recognizing a self antigen. Whereas B-lymphocytes produce antibodies, thymus-derived or "T-cells" are associated with cell-mediated immune functions. T-cells recognize antigens presented on the surface of cells and carry out their functions with these "antigen-presenting" cells.

Various markers have been used to define human T cell populations. CD4 is a non-polymorphic surface glycoprotein receptor with partial sequence identity to immunoglobulins. CD4 receptors define distinct subsets of mature peripheral T cells. In general, CD4 T cells express helper or regulatory functions with B cells in immune responses, while T cells express the CD8 surface antigen function as cytotoxic T cells and have suppressive effects in immune responses. The CD4 receptor consists of a signal peptide, a 370 amino acid extracellular region containing four tandem immunoglobulin-like domains ($V_1$–$V_4$), a membrane spanning domain, and a charged, intracellular region of forty (40) residues.

Since T-cell receptors are thought to augment or modulate T-cell response, they present a potential target for immunological intervention. One approach to the treatment of autoimmune disorders involves monoclonal antibodies specific for CD4 receptors. Murine anti-CD4 monoclonal antibodies appear useful in the treatment of rheumatoid arthritis as disclosed in Hertzog, C. et al. *Lancet*, page 1461 (Dec. 19, 1987). Murine antibodies, however, have characteristics which may severely limit their use in human therapy. As foreign proteins, murine antibodies may elicit immune reactions that reduce or destroy their therapeutic efficacy and/or evoke allergic or hyper-sensitivity reaction in patients. The need for readministration of such therapeutic modalities in autoimmune disorders increases the likelihood of these types of immune reactions.

Chimeric antibodies consisting of non-human antigen binding regions joined to human constant regions have been suggested as a means to circumvent the immunogenicity of murine antibodies. See e.g. *PNAS*, 81:6851 (1984) and PCT Application No. PCT/GB85 00392. Since the constant region is largely responsible for immunogenicity of an antibody molecule, chimeric antibodies with constant regions of human origin should be less likely to evoke an anti-murine response in humans. However, it is unpredictable whether the joining of a human constant region to a nonhuman antigen binding region of a desired specificity will reduce immunoreactivity and/or alter the binding capabilities or the biological activity of the resulting chimeric antibody. Furthermore, immunoglobulin constant regions exist as a variety of isotypes, which are responsible for different effector functions. Therefore the biological activity of a chimeric antibody will depend on the isotype of the constant regions as well as the nature of the antigen-binding regions.

Not all anti-CD4 monoclonal antibodies bind to the same CD4 site or domain, and the site to which a particular monoclonal antibody binds may significantly affect its biological activity, e.g., its immunomodulatory activity, or its ability to block the binding of HIV to CD4 cells, for example.

SUMMARY OF THE INVENTION

This invention pertains to chimeric antibodies for a CD4 receptor comprising a variable or antigen binding region of a non-human origin specific for CD4 receptor and a constant region of human origin, pharamaceutical compositions containing them, and methods for their use in the treatment of diseases and disorders mediated by CD4 positive cells. These antibodies are useful as therapeutic agents for autoimmune disorders, and other diseases or disorders mediated by CD4 positive cells.

BRIEF DESCRIPTION OF THE FIGURE

The FIGURE shows the plasmids for expression of the chimeric chains of the chimeric anti-CD4 antibody.

DETAILED DESCRIPTION OF THE INVENTION

The chimeric anti-CD4 immunoglobulins of the invention are comprised of individual chimeric heavy and light immunoglobulin chains. The chimeric heavy chain is comprised of an antigen-binding region derived from the heavy chain of a non-human antibody specific for a CD4 receptor linked to a human heavy chain constant region. The human heavy chain constant region is preferably of the IgG1 isotype. The chimeric light chain comprises an antigen binding region derived from the light chain of the non-human antibody linked to a human light chain constant region. The human light chain constant region is preferably of the Kappa isotype.

The present immunoglobulins can be monovalent, divalent or polyvalent. Monovalent immunoglobulins are dimers (HL) formed of a chimeric heavy chain associated through disulfide bridges with a chimeric light chain. Divalent immunoglobulins are tetrameres ($H_2L_2$) formed of two dimers associated through at least one disulfide bridge. Such divalent immunoglobulins are preferred for biological activity. Polyvalent immunoglobulins can also be produced, for example, by employing heavy chain constant regions that aggregate (e.g. IgM heavy chains). Chimeric immunoglobulin fragments such as Fab, Fab', or F(ab')$_2$ can also be produced, and may be particularly useful for some applications. The non-human antigen binding regions of the chimeric immunoglobulin are derived from immunoglobulins specific for CD4 receptors. Preferred for biological activity are antibodies of the invention that exhibit high affinity binding to a CD4 site encompassing residues within both the $V_1$ and the $V_2$ domains. Preferred are antibodies of the invention that exhibit high affinity binding to CD4, preferably a Ka of at least $10^8 M^{-1}$, more preferably at least $10^9 M^{-1}$.

The chimeric anti-CD4 monoclonal antibodies of the invention will preferably bind specifically (with high affinity) to a site encompassing residues in both the extracellular $V_1$ and $V_2$ domains, a site distinct from the Leu 3a site and the OKT4 site.

A preferred chimeric murine-human MAb of the invention, designated cM-T412, and murine antibody M-T151 disclosed in *J. of Autoimmunity* 2, 627–642 (1989) are believed to be directed to substantially the same CD4 binding regions. The binding specificity of M-T151 for CD4 has been mapped to an epitope encompassing residues in both the extracellular $V_1$ and $V_2$ domains of the CD4 protein by crossblocking analyses and specific binding to truncated recombinant CD4. Peterson et al., *Cell* 54:65–72 (1988); Ashkenzi et al., *Proc. Natl. Acad. Sci.* USA 87:7150–7154 (1990); Healey et al., *J. Ex. Med.* 172:1233–1242 (October 1990) and Sattentau et al., *J. Ex. Med.* 170:1319–1334 (October 1989(; Ryu et al., *Nature* 348:419–426 (1990) and Wang et al. *Nature* 348:411–418 (1990) Mapping of anti-CD4 monoclonal antibodies to the CD4 receptor is complicated by the fact that many important CD4 epitopes appear to be non-linear, conformational epitopes. Much information about CD4 epitopes comes from cross blocking studies and other analytical procedures as described in the foregoing references, the teachings of which are hereby incorporated herein by reference.

A competition study was carried out to compare CD4 binding of murine M-T412 and murine M-T151. The experiment was performed two ways: (1) 125I M-T412 competing with increasing concentrations of unlabeled M-T412 and M-T151; and (2) 126I M-T151 competing with increased concentrations of unlabeled M-T412 and M-T151. Results indicated that M-T151 and M-T412 cross compete for binding to CEM cells to the same extent and with similar binding kinetics. This suggests that the most efficient inhibition results from direct competition for the same or adjacent epitopes. Sattentau et al., *Science* 232:1120–1123 (1986) Preliminary cross blocking data with a panel of anti-CD4 monoclonal antibodies suggest that the epitopes to which M-T412 and M-T151 are directed are substantially the same but probably not identical. Accordingly, a preferred chimeric murine-human anti-CD4 antibody of the invention is one which comprises murine variable regions substantially similar to those of murine clones M-T412 or M-T151, most preferably an intact divalent immunoglobulin which also comprises a human Fc regions of the IgG1 isotype.

The present cM-T412 chimeric anti-CD4 monoclonal antibody is further preferred as being directed to a conserved CD4 epitope. A binding study of cM-T412 with peripheral blood from 50 normal donors representing both sexes and an ethnic mix, suggested that cM-T412 binds to a conserved epitope, since all samples exhibited the same magnitude and kinetics of immunoreactivity.

Preferred chimeric anti-CD4 monoclonal antibodies of the invention are those which will competitively inhibit the binding to CD4 receptor of a chimeric anti-CD4 monoclonal antibody substantially similar to cM-T412. Quantities of the cM-T412 antibody, designated "c128", are deposited as a reference standard at Centocor, Malvern, Pa., USA, and at the American Type Culture Collection (ATCC), Rockville, Md., USA on Dec. 21, 1990 and received ATCC No. 40942. cM-T412 (c128) is a chimerical monoclonal antibody produced by cell line C128A, which is on deposit as a master cell bank in the Centocor Cell Culture Research & Development Depository, Malvern, Pa., USA, and at Centocor BV, Leiden, The Netherlands. The cM-T412 chimeric murine-human monoclonal antibody is a specifically preferred embodiment of the invention. The teaching of Muller, R. (1983), "Determination of affinity and specificity of anti-hapten antibodies by competitive radioimmunoassay", *Methods in Enzymology* U92:589–601, with respect to methods for determining competitive inhibition of monoclonal antibody binding, is hereby incorporated herein by reference.

Preferred immunoglobulins are produced by antibody-producing cell lines which may be hybrid cell lines commonly known as hybridomas. The hybrid cells are formed by the fusion of an anti-CD4 antibody producing cell and an immortalizing cell line, that is, a cell line which imparts long term tissue culture stability to the hybrid cell. In the formation of the hybrid cell lines, the first fusion partner—the anti-CD4 antibody producing cell—may be a spleen cell of an animal immunized against a CD4 positive T cell or a biological preparation comprising CD4. Alternatively, the anti-CD4 producing cell may be a B lymphocyte obtained from the spleen, lymph nodes or other tissue. The second fusion partner—the immortal cell—may be a lymphoblastoid cell or a plasmacytoma cell such as a myeloma cell, itself an antibody producing cell, but also maligant.

Murine hybridomas which produce CD4 specific monoclonal antibodies are formed by the fusion of mouse myeloma cells and spleen cells from mice immunized against human CD4 positive T cells, purified CD4, or other biological preparations comprising CD4, or a component thereof. For example, a preparation comprising P815 mastocytoma cells transfected with human CD4 cDNA was used successfuly in the Examples. To immunize the mice, a variety of different protocols may be followed. For example, mice may receive primary and boosting immunizations of CD4 positive T cells or recombinant CD4. The fusions are accomplished by standard procedures well known to those skilled in the field of immunology. Kohler and Milstein, *Nature*, 256:495–497 (1975) and Kennet, *Monoclonal Antibodies* (Kennet et al., Eds. pp. 365–367, Plenum Press, N.Y., 1980). Several murine CD4 specific monoclonal antibodies are described in Hertzog, C. et al., supra; Hertzog, C. et al. *J. Autoimmunity* 2:627–642 (1989) and Walker et al. *J. Autoimmunity* 2:643–649 (1989).

Another way of forming the anti-CD4 producing cell line is by transformation of antibody producing cells. For example, an anti-CD4 producing B lymphocyte may be infected and transformed with a virus such as Epstein-Barr virus in the case of B lymphocytes to yield an immortal anti-CD4 producing cell, See e.g., Kozbor and Roder, *Immunology Today*, 4(3):72–79 (1983). Alternatively, the B lymphocyte may be transformed by a transforming gene or transforming gene product.

The CD4 specific monoclonal antibodies are produced in large quantities by injecting anti-CD4 antibody producing hybridomas into the peritoneal cavity of mice and, after appropriate time, harvesting the ascites fluid which contains a high titer of homogeneous antibody and isolating the monoclonal anti-CD4 antibody therefrom. Xenogeneic hybridomas should be injected into irradiated or athymic nude mice. Alternatively, the antibodies may be produced by culturing anti-CD4 producing cells in vitro and isolating secreted monoclonal anti-CD4 antibodies from the cell culture medium.

The CD4 specific chimeric antibodies of the invention are produced by cloning DNA segments encoding the heavy and light chain variable regions of a non-human antibody specific for CD4 and joining these DNA segments to respective DNA segments encoding human heavy and light chain constant regions to produce chimeric immunoglobulin encoding genes. The fused gene constructs coding for the light and heavy chains are assembled in or inserted into expression vectors. The genes are co-transfected into a lymphoid recipient cell (e.g. a myeloma cell) where the immunoglobulin protein can be synthesized, assembled and secreted. The transfected receipient cells are cultured and the expressed immunoglobulins are collected.

Preferably, the antigen binding regions will be of murine origin because murine antibodies against CD4 are available or can be readily produced in murine systems. Other animal or rodent species provide alternative sources of antigen binding regions.

The constant regions of the chimeric antibodies are derived from human immunoglobulins. The heavy chain constant region can be selected from any of the five isotypes—alpha, delta, epsilon, gamma or mu. Further, heavy chains of various subclasses (such as the IgG subclasses of heavy chains) are responsible for different effector functions and thus, by choosing the desired heavy chain constant region, chimeric antibodies with desired effector function can be produced. Preferred constant regions are gamma 1 (IgG1), gamma 3 (IgG3) and gamma 4 (IgG4). More preferred is an Fc region of the gamma 1 (IgG1) isotype. The light chain constant region can be of the kappa or lambda type, preferably of the kappa type.

In order to assess the effect of human heavy chain constant region isotype on the activity of chimeric anti-CD4 antibodies of the invention, mouse-human chimeric CD4 IgG1 and IgG4 antibodies were constructed with murine M-T412 variable regions and human Fc constant regions. $F(ab')_2$ and Fab fragments of the murine (M-T412) and chimeric γ1 (cM-T412) antibodies were generated by enzymatic digestion. The cM-T412γ1 and its fragments retained the affinity and specificity of the parent murine antibody.

The ability of intact CD4 antibody or antibody fragment to affect CD4$^+$ T-cell activity was evaluated in in vitro assays of Ig production by pokeweed mitogen-stimulated cells, level of sIL-2 receptor production by phytohemagglutinin-stimulated PBMCs (peripheral blood mononuclear cells), and cell proliferation in response to: tetanus toxoid, anti-CD3 antibodies, and mixed lymphocyte culture. Representative findings are seen with tetanus toxoid where the cM-T412γ1 MAb, the intact divalent ($H_2L_2$) immunoglobulin of the γ1 isotype, inhibited the proliferation of PBMCs by 90% at 0.1 µ/ml. In contrast, the cM-T412γ4 achieved a maximum of 65% inhibition even at 10 µg/ml, whereas the cM-T412γ1 Fab required 100 µg/ml for similar inhibition. These data show that the intact chimeric mouse-human anti-CD4γ1 antibody of the invention exhibits superior down regulation of T-cell function, with a strong contribution by the γ1 $F_c$ region. These results support the potential clinical utility of a divalent chimeric mouse-human anti-CD4 γ1 monoclonal antibody in autoimmune disease or disorders.

In general, the chimeric antibodies are produced by preparing, for each of the light and heavy chain components of the chimeric immunoglobulin, a fused gene comprising a first DNA segment that encodes at least the functional portion of the CD4-specific variable region of non-human origin linked (e.g. functionally rearranged variable region with joining segment) to a second DNA segment encoding at least a biologically functional part of a human constant region. Each fused gene is assembled in or inserted into an expression vector. Recipient cells capable of expressing the gene products are then transfected with the genes. The transfected recipient cells are cultured under conditions that permit expression of the incorporated genes and the expressed immunoglobulins or immunoglobulin chains are recovered.

Genes encoding the variable region of Ig light and heavy chains can be obtained from lymphoid cells that produce the CD4-specific antibodies. For example, the hybridoma cell lines that produce antibody against CD4 provide a source of immunoglobulin variable region for the present chimeric antibodies. Other rodent cell lines are available. Cell lines can be produced by challenging a rodent with a CD4-positive cell or a CD4 containing component or fraction of a CD4 positive cell, forming fused hybrid cells between antibody-producing cells and a myeloma cell line, cloning the hybrid and selecting clones that produce antibody against the CD4 receptor. Antibodies can be further characterized as to epitope specificity (high affinity binding), as described in Sattentau et al., supra, the teachings of which are hereby incorporated by reference.

It is contemplated that further "humanization" of the monoclonal antibodies of the invention may be accomplished by forming "mosaic" antibodies in which human sequences are also inserted into the variable region. For example, the variable regions of both mouse and human antibodies comprise four framework residues (FRs). Within the FRs are three complementarity determining residues (CDRs) which are responsible for antigen binding. A human-mouse mosaic having the desired binding characteristics may be made by inserting mouse CDR sequences within human framework residues. Such mosaic variants are contemplated equivalents of the chimeric immunoglobulins of the invention, as are partial chimeric immunoglobulins, e.g., in which only the heavy chain constant region of murine origin has been replaced by an equivalent sequence of human origin, or variants wherein one or more amino acids have been changed by directed mutagenesis.

Constant regions can be obtained from human antibody-producing cells by standard cloning techniques. Alternatively, because genes representing the two (2) classes of light chains and the five (5) classes of heavy chains have been cloned, constant regions of human origin are readily available from these clones. Chimeric antibody binding fragments such as $F(ab')_2$ and Fab fragments can be prepared by designing a chimeric heavy chain gene in truncated form. For example, a chimeric gene encoding a $F(ab')_2$ heavy chain portion would include DNA sequences encoding the $CH_1$ domain and hinge region of the heavy chain.

The fused genes encoding the light and heavy chimeric chains (or portions therof) can be assembled in two different expression vectors that can be used to co-transfect a recipient cell. Each vector contains two (2) selectable genes—one for selection in a bacterial system and one for selection in a eukaryotic system—each vector having a different pair of genes. These vectors allow production and amplification of the fused genes in bacterial systems, and subsequent co-transfection of eukaryotic cells and selection of the co-transfected cells. Examples of selectable genes for the bacterial system are the genes that confer ampicillin resistance and the gene that confers chloramphenicol resistance. Two selectable genes for selection of eukaryotoic transfectants are preferred: (i) the xanthine-guanine phosphoribosyltransferase gene (gpt), and (ii) the phosphotransferase gene from Tn5 (designated neo). Selection with gpt is based on the ability of the enzyme encoded by this gene to use xanthine as a substrate for purine nucleotide synthesis; the analogous endogenous enzyme cannot. In a medium containing xanthine and mycophenolic acid, which blocks the conversion of inosine monophosphate to xanthine monophosphate, only cells expressing the gpt gene can survive. The product of the neo blocks the inhibition of protein synthesis in eukarytoic cells caused by the antibiotic G418 and other antibiotics of its class. The two selection procedures can be used simultaneously or sequentially to select for the expression of immunoglobulin chain genes introduced on two (2) different DNA vectors into a eukaryotic cell.

Alternatively, the fused genes encoding the chimeric light and heavy chains can be assembled on the same expression vector.

The preferred recipient cell line is a myeloma cell. Myeloma cells can synthesize, assemble and secrete immunoglobulins encoded by transfected Ig genes. Further, they possess the mechanism for glycosylation of the immunoglobulin. A particularly preferred recipient cell is the Ig-non-producing myeloma cell Sp2/0. The cell produces only immunoglobulin encoded by the transfected immunoglobulin genes. Myeloma cells can be grown in culture or in the peritoneum of mice where secreted immunoglobulin can be obtained from ascites fluid. Other lymphoid cells such as B lymphocytes or hybridoma cells can serve as suitable recipient cells.

Several methods exist for transfecting lymphoid cells with vectors containing immunoglobulin encoding genes. A preferred way of introducing DNA into lymphoid cells is by electroporation. In this procedure, recipient cells are subjected to an electric pulse in the presence of the DNA to be incorporated. See e.g., Potter et al., PNAS 81:7161 (1984). Another way to introduce DNA is by protoplast fusion. In this method, lysozyme is used to strip cell walls from catarrhal harboring the recombinant plasmid containing the chimeric Ig gene. The resulting spheroplasts are fused with myeloma cells with polyethylene glycol. Another technique that can be used to introduce DNA into many cell types is calcium phosphate precipitation.

The chimeric immunoglobulin genes can be expressed in nonlymphoid mammalian cells or in organisms such as bacteria or yeast. When expressed in bacteria, the immunoglobulin heavy chains and light chains become part of inclusion bodies. Thus, the chains must be isolated and purified and then assembled into functional immunoglobulin molecules.

The chimeric CD4 specific antibodies of the invention are useful as therapeutic agents for autoimmune disorders such as rheumatoid arthritis, SLE, multiple sclerosis and myesthenia gravis, as well as other disorders mediated by CD4+ cells. The antibody is administered to a mammal suffering from such a disorder in a therapeutically effective amount sufficient to alleviate the disorder.

The chimeric monoclonal antibodies of the invention will usually be formulated for therapeutic use as a pharmaceutical composition comprising appropriate carriers, excipients, and other pharmaceutically acceptable ingredients, as is known to those of skill in the art of pharmaceutics. Like other proteinaceous materials, a monoclonal antibody preparation will frequently be formulated as a sterile, non-pyrogenic composition for parenteral administration; however, any pharmaceutically acceptable route and method of administration that brings that active moiety into contact with its site of action may be used, such as those described in a standard reference text in this field, e.g., *Remington's Pharmaceutical Sciences*, the teachings of which are hereby incorporated by reference.

The invention is further described by the following examples, wherein all parts and percentages are by weight and degrees are Celsius, unless otherwise stated.

EXEMPLIFICATION

Murine Hybridoma M-T412

A murine hybridoma designated M-T412 was one of a panel of murine anti-CD4 monoclonal antibodies obtained from G. Riethmuller, Univ. of Munich, Munich, Germany. The M-T412 clone was produced from spleen cells of mice immunized with P815 mastocytoma cells transfected with human CD4 cDNA. The mice were additionally boosted with recombinant CD4. The M-T412 antibody was of high affinity for CD4 receptor bearing CEM cells and of similar binding specificity to a murine anti-CD4 monoclonal antibody designated MT151 (described in papers by Herzog et al. and Walker et al., supra.) The details of the preparation of murine hybridoma M-T412 are as follows: The hybridoma giving rise to the murine M-T412 antibody was derived from a fusion performed in the laboratory of Dr. Peter Rieber, Institute for Immunologie, Universitat Munchen, Munich, Germany.

BALB/c mice originally obtained from the Centralinstitut fur Versuchstierzucht (Hanover, Germany) and bred at the Institute for Immunologie, Munich, Germany were immunized with P815 cells (obtained from Van Pel, Ludwig Institute for Cancer Research, Brussels, Belgium) transfected with cloned DNA representing a full length copy of the gene encoding human CD4. The CD4 clone was derived from a cDNA library provided by D. Littman (University of California, San Francisco, Calif., USA). The cDNA was cleaved with Xho II, cloned in pKSv10 and the fragment representing the full length CD4 gene was transfected into P815 cells by Y. Tabaycewski and E. Weiss, Institute for Immunologie, Munich.

A BALB/c mouse was immunized intrasplenically with $5 \times 10^6$ P815-CD4 cells. Forty days later the mouse was injected again intrasplenically with $5 \times 10^6$ P815-CD4 cells. Three days later the mouse was sacrificed, the spleen was removed and a single cell suspension was obtained by mechanical disaggregation. The spleen cells were resuspended in RPMI 1640 containing 20% (v/v) fetal bovine serum and 10% (v/v) DMSO and cryopreserved in liquid nitrogen.

The cells were subsequently thawed and $3.2 \times 10^7$ spleen cells were fused with $2.4 \times 10^7$ P3x63Ag8.653 (0.653) myeloma cells (provided by H. Lemke, Cologne, Germany). The spleen cells and 0.653 cells were mixed and centrifuged for 10 min at 1600 rpm. The supernatant was removed and the pellet was resuspended in 5 mL prewarmed, serum free DMEM, centrifuged at 1200 rpm, for 5 min. The supernatant was removed, and 1 ml 50% (w/v) PEG 4000 in RPMl 1640 (prewarmed to 37° C.) was added dropwise. The cells were then centrifuged for 1 min at 1000 rpm followed by addition of 10 mL RPMI 1640 (37° C.) without serum dropwise over 5 min. The pelle was resuspended, another 10 ml of medium added and the sample centrifuged fro 10 min at 1600 rpm. The supernatant was removed and the cells were resuspended in HAT medium (RPMI 1640 supplemented with 10% (v/v) fetal bovine serum; 100 µ/mL penicillin; 100 µg/mL streptomycin; $6.4 \times 10^{-5}$ M thymidine. The fused cells were seeded at 100 µL/well into each well of 96-well plates. Fifty thousand (50,000) BALB/c-DBA f1 peritoneal exudate cells in 100 µL were added to each well. The cells were fed with HT medium (HAT with aminopterin) after 4 and 7 days and assayed on day 10–14.

Four-hundred and fifty (450) growth positive wells were screened against normal human peripheral blood mononuclear cells by fluorescence microscopy. From this fusion, 3 anti-CD4 hybridomas were obtained and designated M-T412, M-T413, and M-T414.

The M-T412 cell line was grown in Iscove's modification of Dulbecco's modified Eagle's Minimum Essential Medium (IDMEM supplemented with 5% (v/v) fetal bovine serum, 2 mM L-glutamine, 1 mM sodium pyruvate and Eagle's Non-Essential Amino Acids). A cell bank created from this culture was used for production of the chimeric anti-CD4 monoclonal antibody.

General Strategy for Production of Chimeric Anti-CD4 Monoclonal Antibodies

The strategy for cloning the variable regions for the heavy and light chain genes from the hybridoma M-T412 was based upon the linkage in the genome between the variable region and the corresponding J (joining) region for functionally rearranged (and expressed) Ig genes. J region DNA probes can be used to screen genomic libraries to isolate DNA linked to the J regions; DNA in the germline configuration (unrearranged) would also hybridize to J probes, but is not linked to a variable region sequence and can be indentified by restriction enzyme analysis of the isolated clones.

The cloning strategy, therefore, was to isolate variable regions from rearranged heavy and light chain genes using $J_H$ and $J_K$ probes. These clones were tested to see if their sequences were expressed in the 412 hybridoma by Northern analysis. Those clones that contained expressed sequence were cloned into expression vectors containing human constant regions and transfected into mouse myeloma cells to determine if an antibody was produced. The antibody from producing cells was then tested for binding specificity and functionality compared to the 412 murine antibody.

MATERIALS AND METHODS

Light Chain Genomic Library Construction

To isolate the light chain variable region gene from the 412 hybridoma, a size-selected genomic library was constructed using the phage lambda vector charon 27. High molecular weight DNA was isolated from 412 hybridoma cells and digested to completion with restriction endonuclease HindIII. The DNA was then fractionated on a 0.8% agarose gel and the DNA of size range 4–6 kb was isolated directly from the gel by electroelution. After phenol/chloroform extraction and ethanol precipitation, the 4–6 kb fragments were ligated with lambda charon 27 arms and packaged into phage particles in vitro using Gigapack Gold from Stratagene. This library was screened directly at a density of approximately 20,000 plaques per 150 mm petri dish using a $^{32}$P-labeled $J_K$ probe. Plaque hybridizations were carried out in 5×SSC, 50% formamide, 2× Denhardt's reagent, 200 µg/ml denatured salmon sperm DNA at 42 degrees for 18–20 hours. Final washes were in 0.5×SSC, 0.1% SDS at 65 degrees. Positive clones were identified after auto-radiography.

Heavy Chain Genomic Library Construction

To isolate the variable region gene for the 412 heavy chain, a genomic library was constructed in the lambda vector EMBL-3. High molecular weight DNA was partially digested with restriction endonuclease Sau3A and size-fractioned on a 10–40% sucrose density gradient. DNA fragments of approximately 15–23 kb were ligated with EMBL-3 arms and packaged into phage particle in vitro using Gigapack Gold. This library was screened at a density of 30,000 plaques per 150 mm plate using a $J_H$ probe. Hybridization and wash conditions were identical to those used for the light chain library.

DNA Probes

The mouse heavy chain $J_H$ probe is a 2 kb BamHI/EcoRI fragment containing both J3 and J4 segments. The mouse light chain $J_K$ probe is a 2.7 kb HindIII fragment containing all five $J_K$ segments. $^{32}$P-labeled probes were prepared by random priming using a kit obtained from Boehringer Mannheim. Free nucleotides were removed by centrifugation through a Sephadex G-50 column. The specific activities of the probes were approximately $10^9$ cmp/µg.

Northern Analysis

Ten (10) µg total cellular RNA was subjected to electrophoresis on 1% agarose/formaldehyde gels (Maniatis, et al., *Molecular Cloning*) and transferred to nitrocellulose. Blots were hybridized with random primed DNA probes in 50% formamide, 2× Denhardt's solution, 5×SSC, and 200 µg/ml denatured salmon sperm DNA at 42 degrees for 10 hours. Final wash conditions were 0.5×SSC 0.1% SDS at 65 degrees.

DNA Transfection Using Electroporation

Plasmid DNA to be transfected was purified by centrifuging to equilibrium in ethidium bromide/cesium chloride gradients two (2) times. Ten (10)-50 µg of plasmid DNA was added to $10^7$ SP2/0 cells in Hanks salts medium and the mixture placed in a Biorad electroporation apparatus. Electroporation was at 200 volts and the cells were plated out in 96 well microtiter plates. Appropriate drug selection was applied after 48 hours and drug resistant colonies were identified after 1–2 weeks.

Quantitation of Antibody Production

Tissue culture supernatant was analyzed for IgG protein content by Elisa assay using standard curves generated with purified IgG. Concentration of chimeric 412 antibody with human constant regions was determined using goat anti-human IgG Fc antibody-coated microtiter plates and alkaline phosphatase conjugated goat anti-human IgG Fc or goat anti-human IgG (H+L) antibody.

Tissue culture supernatant was loaded onto a protein A-sepharose column. The chimeric antibody was eluted from the protein A column with a sodium citrate pH gradient from pH 6.5 to pH 3.5. The purified antibody was concentrated using a Diaflo YM100 ultrafiltration membrane. Antibody concentration was measured by determining the absorbance at 280 nm.

Indirect Cell Binding Assay on CEM Cells

All samples and standards were diluted to 100 µg/ml with 0.3% gelatin-PBS-0.2% azide. Gelatin-PBS-azide was added to each well of a 96 well microtiter plate; the first column of the plate was left empty An aliquot (150 µl) of each sample and standard was added in duplicate to the (empty) first column of the 96 well plate. Twelve serial 1:4 dilutions were performed by transferring 40 ul each time.

$^{125}$I goat anti-human F(ab')2 was diluted to approximately 300,000 cpm/100 µl (5–10 uCi/µg) in gelatin-PBS-azide.

CEM cells were centrifuged at 1000 rpm, 15 min, the supernatant was discarded and the pellet was resuspended with Hanks buffered saline. Cells were washed twice and a cell count was performed with Trypan Blue. Cells were plated at $7 \times 10^5$/well in a V-bottom 96 well polyvinyl plate. To obtain an even distribution of cells, the cell suspension was poured into a petri plate and the plate was swirled gently with one hand while pipetting with the other hand. The plate was centrifuged at 1500 rpm for 5 min and the supernatant was aspirated.

Aliquots (100 µl) of the antibody dilutions were added to each well. The pellet was resuspended by gently pipetting up and down. Cells were incubated for 3 hr at 4° C., then centrifuged at 1500 rpm for 5 min, and the supernatant was aspirated and the pellet was resuspended in 200 µl gelatin-PBS-azide. A spin-wash was performed twice. An aliquot (100 µl ) of the 125-I goat anti-mouse F(ab')2 was added to each well. The pellet was resuspended and incubated for 2 hr at room temperature. Cells were spin washed twice and the supernatant was aspirated off. Each well was counted in a gamma counter. The bound counts per minute (cmp) were plotted on the ordinate, antibody concentration was plotted on the abscissa and the concentration at half maximal binding was determined.

Results

Cloning of the CD4-Specific Variable Gene Regions

Several positive clones were isolated from the heavy and light chain libraries after screening approximately one million plaques using the $J_H$ and $J_K$ probes, respectively. Following at least three (3) rounds of plaque purification, bacteriophage DNA was isolated for each positive clone, digested with either EcoRI (heavy chain clones) or HindIII (light chain clones) and fractionated on 1% agarose gels. The DNA was transferred to nitrocellulose and the blots were hybridized with $J_H$ (heavy chain) or $J_K$ (light chain) $^{32}$P-labeled DNA probes. For the heavy chain, several clones were obtained that contained 5.5 kb Eco RI DNA fragments that hybridized to the $J_H$ probe. The $J_K$ probe hybridized to a 5.4 kb fragment present in several light chain clones.

Cloned DNA corresponding to the authentic heavy and light chain variable regions from the 412 hybridoma should hybridize to mRNA isolated from the hybridoma. Non-functional DNA rearrangements at either the heavy or light chain loci should not be expressed. The subcloned fragments were labeled with $^{32}$-P by random priming and hybridized to northern blots containing total RNA derived from 653 (the fusion partner of the 412 hybridoma) or from 412. The 5.5 kb EcoRI heavy chain fragment hybridized with a 2 kb EcoRI heavy chain fragment in 412 RNA, but not in 653 RNA. Similarly, the 5.4 kb light chain HindIII fragment hybridized with a 1250 by mRNA in 412 RNA, but not in 653 RNA. These are the correct sizes for heavy and light chain mRNAs respectively. Because the cloned DNA fragments contain sequences expressed in the 412 hybridoma, these data suggest that these are the correct variable region sequences from the 412 hybridoma. The final functional test, however, is the demonstration that these sequences, when combined with the appropriate constant region sequences, are capable of directing the synthesis of an antibody with a specificity and affinity similar to that of the murine 412 antibody.

Vectors and Expression Systems

The putative light and heavy chain V genes cloned from the 412 hybridoma were joined to human kappa and G1 constant region genes in expression vectors. The 5.5 kb EcoRI fragment corresponding to the putative heavy chain V region gene from 412 was used to replace the 17-1A $V_H$ EcoRI fragment of the previously described vector pSV2ΔHgpt17-1A$V_H$-hCG1 (Sun, L. et al., PNAS 84, p. 214–218 (1987)) to yield p412HG1apgpt. For the light chain, two (2) different constructions were made. In the first construction, the 5.4 kb putative light chain fragment from 412 was used to replace the 17-1A HindIII fragment of pSV184-ΔHneo17-1AVKhCK to yield p412HuKcmneo. In the second construction, the 5.4 kb HindIII fragment from 412 was cloned into a similar vector to pSV184ΔHneo17-1AVhCK except that the selectable marker for mammalian cells was Ecogpt instead of neo. The resulting plasmid was designated p412HuKapgpt. A plasmid was also constructed containing both heavy and light chain genes in the same plasmid, and was designated p412-DP. The 412 expression plasmids are shown in FIG. 1.

To express the chimeric heavy and light chain genes, various combinations of the expression plasmids were transfected into the non-producing mouse myeloma cell line SP2/0. The heavy chain vector was co-transfected with either the neo or gpt version of the light chain vector, and p412-DP was transfected alone. Mycophenolic acid selection was applied after 24 hours; for cotransfections with neo and gpt vectors, selection with both mycophenolic acid and G418 was used. Resistant colonies were expanded to stable cell lines and tissue culture supernatant from these cell lines was tested for antibody using an ELISA assay with goat anti-human IgG Fc antibody and goat anti-human H+L conjugated with alkaline phosphatase (Jackson Laboratories). A cell line designated JL3A3 was chosen for further study. Cell line JL3A3 (also referred to as C128A (JL3A3.13) was deposited on Sep. 10, 2004 at the American Type Culture Collection Corporation, 10801 University Boulevard, Manassas, Va. 20110-2209, U.S.A. in accordance with the terms of the Budapest Treaty under ATCC® Accession No. PTA-6196.

The chimeric 412 antibody was purified from tissue culture supernatant of cell line JL3A3 by Protein A Sepharose chromatography. 190 mls of supernatant was adjusted to 0.1 M Tris, 0.002 M EDTA, pH 8.0 and loaded on a 12 ml Protein A Sepharose column equilibrated in 0.1 M Tris, 0.002 M EDTA, pH 8.0. The column was Washed to baseline, and the IgG was eluted with a pH gradient from 0.1 M citrate pH 6.5 to 0.1 M citrate pH 3.5, with the IgG peak eluting at approximately pH 4.0. The peak was pooled, neutralized with 1 M Tris, diafiltered into PBS, and 0.2 micron filtered. 5.4 mg was recovered (approximately 28 ug/ml starting supernatant).

The IgG was evaluated for purity by HPLC and SDS-PAGE. HPLC analysis on GF-250 gel filtration showed a single peak with an apparent molecular weight of approximately 150,000. SDS-PAGE on Pharmacia Phastgel 10–15% (4 ml samples) visualized with Coomasie stain also showed a clean preparation of the same molecular weight.

The purified IgG was evaluated for immunoactivity in an indirect cell binding assay on CEM cells. CEM cells display the CD4 receptor on their surface. Chimeric 7E3 G1, an irrelevant antibody, as run as a negative control. Relative affinity values were determined from the inverse of the concentration (M) at half maximal binding. The values obtained are as follows:

| Sample | Tracer | Relative Affinity |
| --- | --- | --- |
| cC123B JL3A3 (chimeric 412) | anti human F (ab')$_2$ | $2.5 \times 10^9$ M$^{-1}$ |
| cC123B JL3A3 (chimeric 412) | anti human Fc | $8.0 \times 10^9$ M$^{-1}$ |
| c123 Clinical Vial (murine 412) | anti mouse F(ab')$_2$ | $6.5 \times 10^9$ M$^{-1}$ |

The data demonstrate that chimeric anti-CD4 IgG1 binds to CEM cells with an affinity similar to the murine anti-CD4 antibody. This indicates that the murine and chimeric antibodies have similar affinities for the human CD4 receptor.

Biological Information

To assess safety, pharmacokinetics, and CD4 effects, a preferred chimeric anti-CD4 monoclonal antibody of the invention (cM-T412) was administered intravenously (IV) for seven days at a dose of 5 mg/kg/day to four chimpanzees. The antibody was well tolerated and circulating CD4 cell number was markedly decreased from the first dose through 2–3 weeks after the last dose. CD4 positive cells increased in number 3–4 weeks post dose, but remained depressed in treated animals relative to saline treated controls for 3–4 months. No anti-chimeric antibody response was detected. The prolonged depletion of circulating CD4+ T-cells with no incidence of adverse effects or immunogenic response supports the potential clinical application of such chimeric anti-CD4 monoclonal antibodies to the treatment of autoimmune disease, such as, for example, rheumatoid and psoriatic arthritis, MS, SLE, and myasthenia gravis.

Significant improvement of symptoms was also observed in a seris of 15 human patients with refractory rheumatoid arthritis treated with single IV doses ranging from 1–200 mg of a preferred chimeric anti-CD4 antibody of the invention, CT-M412. Signficiant decreases in swollen joints and tender joints were observed up to 21 days and 90 days, respectively, post treatment. The antibody was well tolerated, with only transient flu-like symptoms observed. Modest anti-mouse response occurred in 8/15 patients. Sustained decreases in CD4+ T-cells occurred upt o 14 days post treatment, and were present though less pronounced at 35 days. CD8+ cells were also transiently decreased following treatment, but reverted to baseline by 72 hours. Clinical dosage may vary depending on the nature and severity of the condition being treated, as well as the age and weight of the patient and the existence of concurrent conditions; however, single IV doses in the range of 1–20 mg are expected to be clinically useful.

While binding of M-T412 to both CEM and human T lymphocytes can be blocked by M-T151, there are certain functional differences between these antibodies. In vivo evidence includes a report of clinical trials in rheumatoid arthritis patients in whom M-T151 effected improvement in symptoms with only a transiet decrease in circulating CD4+ cells and an increase in CD+8 cells. Herzog et al., *J. Autoimmunity* 2: 627–642 (1989). In contrast, in vivo administration of the cM-T412 antibody results in long-term depletion of CD4+ T cells as well as a depletion of CD8+ T cells. Although this difference in biological activity between the murine antibody, M-T151, and the chimeric antibody, cM-T412, could result in part from the human Fc portion of the chimeric antibody which may better recruit human effector functions, however, clinical reports with chimeric anti-leu3a monoclonal antibody (which like cM-T412 is of the gamma 1 isotype), and well as evidence from in vitro assays of M-T412 and M-T151 suggest that at least some differences in epitope specificity may be involved. For example, in evaluating the effects of antibodies on the proliferation of peripheral blood mononuclear cells (PBMC) in response to tetanus toxoid, the cM-T412 was more effective than the parent murine M-T412; both were more effective than the M-T151 (murine). Since M-T412 and M-T151 are both of the murine G2a isotype, differences between them are most likely due to differences in the Fab regions. Because of its ability to down regulate both CD4 and CD8 subsets of T cells, the chimeric anti-CD4 monoclonal antibody of the invention designated cM-T412 is more preferred. cM-T412 has also been observed to down regulate both activate cell surface IL-2 receptors and soluble IL-2.

EQUIVALENTS

Those skilled in the art will recognize, or be able to ascertain using no more than routine experimentation, many equivalents to the specific embodiments of the invention described herein. Such equivalents are intended to be encompassed by the following claims.

What is claimed is:

1. A CD4-specific chimeric immunoglobulin or chimeric antigen binding fragment thereof, said immunoglobulin or fragment having the epitopic specificity of monoclonal antibody M-T412 and comprising the variable region of monoclonal antibody M-T412 (produced by the cell line ATCC® Accession No. PTA-6196) and at least a portion of a constant region of human origin.

2. A CD4-specific chimeric immunoglobulin fragment, wherein said fragment has the epitopic specificity of monoclonal antibody M-T412 and comprises the variable region of monoclonal antibody M-T412 (produced by the cell line ATCC® Accession No. PTA-6196) and at least a portion of a constant region of human origin.

3. A chimeric an immunoglobulin or chimeric antigen binding fragment thereof, wherein said immunoglobulin or fragment is specific for CD4, has the epitopic specificity of monoclonal antibody M-T412, and comprises:
   a) at least one chimeric heavy chain comprising the heavy chain variable region of monoclonal antibody M-T412 (produced by the cell line ATCC® Accession No. PTA-6196) linked to at least a portion of a human heavy chain constant region, the heavy chain being in association with:
   b) at least one chimeric light chain comprising the light chain variable region of monoclonal antibody M-T412 (produced by the cell line ATCC® Accession No. PTA-6196) linked to at least a portion of a human light chain constant region.

4. A chimeric immunoglobulin Fab, Fab' or F(ab')$_2$ fragment which has the epitopic specificity of monoclonal antibody M-T412 and comprises the variable region of monoclonal antibody M-T412 (produced by the cell line ATCC® Accession No. PTA-6196) and a human constant region.

5. A method of therapy for an autoimmune disorder, comprising administering to a patient a therapeutically effective amount of a CD4-specific chimeric immunoglobulin or chimeric antigen binding fragment of claim 1.

6. The method of claim 5, wherein a chimeric antigen binding fragment is administered.

7. The method of claim 6, wherein the chimeric antigen binding fragment is an Fab fragment, Fab' fragment or F(ab')$_2$ fragment.

8. A CD4-specific chimeric immunoglobulin fragment of claim 2, wherein said fragment is an Fab fragment, Fab' fragment or F(ab')$_2$ fragment.

9. A chimeric immunoglobulin or chimeric antigen binding fragment of claim 3, which is an Fab fragment, Fab' fragment or F(ab')$_2$ fragment.

* * * * *